US00PP09306P

United States Patent [19]

Hanes

[11] Patent Number: Plant 9,306

[45] Date of Patent: Sep. 26, 1995

[54] GERANIUM NAMED 'AMERICANA ROSE SPLASH'

[75] Inventor: Mitchell E. Hanes, Morgan Hill, Calif.

[73] Assignee: Goldsmith Seeds, Inc., Gilroy, Calif.

[21] Appl. No.: 364,874

[22] Filed: Dec. 27, 1994

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Henderson & Sturm

[57] ABSTRACT

A new geranium cultivar particularly distinguished by mid-green foliage without zonation, the flowers are rose with a red splash extending from the center towards the base of each petal, single flower form on large umbels, fast rooting and a robust plant.

1 Drawing Sheet

BACKGROUND OF THE NEW PLANT

The present invention comprises a new and distinct cultivar of geranium, botanically known as *Pelargonium hortorum* Bailey, and hereinafter referred to by the cultivar name Americana Rose Splash. The new cultivar is propagated from a seedling resulting from the cross of a proprietary breeding line known as 2226-6 and the geranium variety known as Rio (U.S. Plant Pat. No. 7,422). The breeding line 2226-6 is a single flower pink with a dark pink basal petal spot (splash). The variety Rio has a dark leaf, single flower, that is pink and also has a basal petal spot (splash).

Americana Rose Splash is a product of a planned breeding program intended to create new geranium cultivars with rose colored flowers with a splash pattern, single petal flower form, mid-green foliage, vigorous growth and superior cutting productivity.

The new cultivar was created in 1991 in Gilroy, Calif. and has been repeatedly asexually reproduced by cuttings in Gilroy, Calif. and Guatemala over a three year period. It has also been trialed at Okemos, Mich. It has been found to retain its distinctive characteristics through successive propagations; and this novelty appears to be firmly fixed.

DESCRIPTION OF PHOTOGRAPH

This new geranium plant is illustrated by the accompanying photographs which show blooms, buds, and foliage of the plant in full color, the colors shown being as true as can be reasonably obtained by conventional photographic procedures.

DESCRIPTION OF THE NEW CULTIVAR

Figure 1:
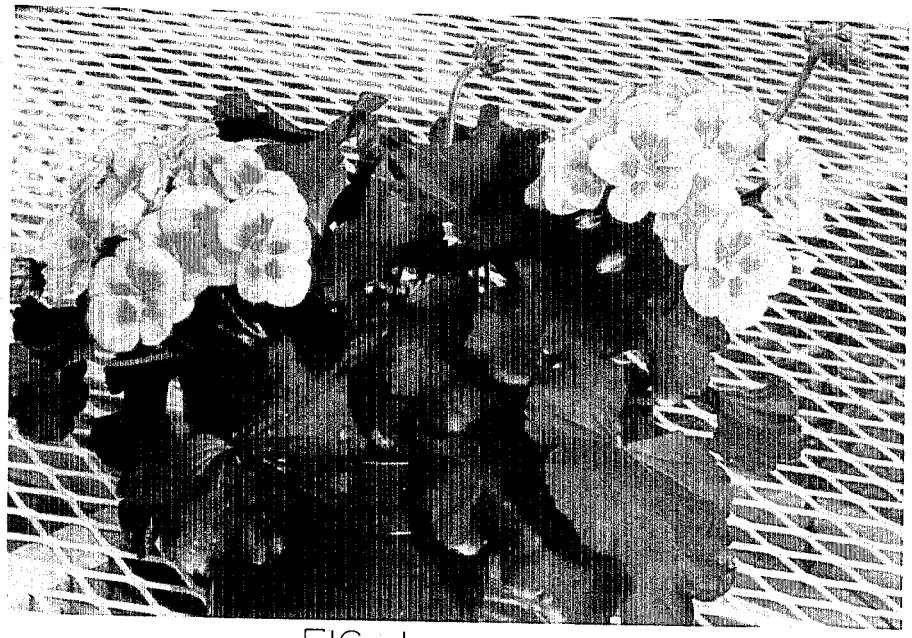
FIG. 1 shows overall plant habit.
Figure 2:
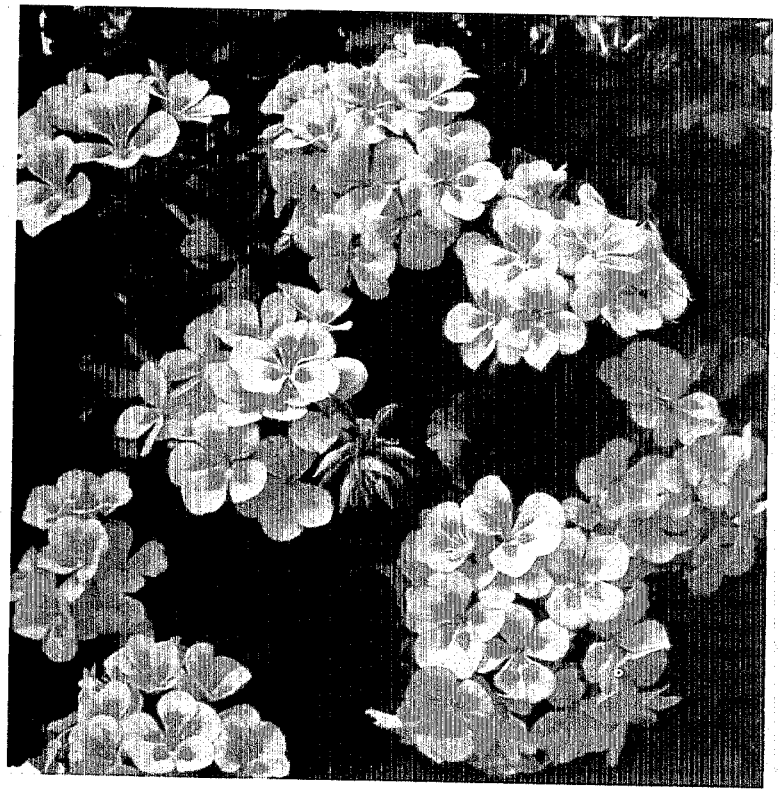
FIG. 2 illustrates the mature flower.

The following detailed descriptions set forth the distinctive characteristics of Americana Rose Splash. The data which defines these characteristics were collected from asexual reproductions carried out by Goldsmith Seeds, Inc. in Gilroy, Calif. The plant history was taken on 24 week old plants, blossomed under natural light in a structure covered with a screen material that provides shade at 55%. Color readings were taken outside (in Gilroy, Calif.) on Aug. 25, 1994 at 10:00 a.m. under indirect ambient light. Color references are primarily to the RHS Colour Chart of The Royal Horticultural Society of London (RHS).

THE PLANT

Classification:

*Botanical.*—*Pelargonium hortorum* Bailey.

*Commercial.*—Zonal geranium.

Form: The plant grows with a rounded habit that is somewhat flat across the top of the plant.

Height: 21–27 cm, as an 18–20 inch containerized plant, excluding blooms.

Strength: Vigorous mid-green plants that have a strong garden performance. Good shipping ability as rooted or unrooted cuttings.

Foliage: Abundant quantity.

Leaves:

*Size.*—Diameter about 8–11 cm.

*Shape.*—Rounded cordate with occasional upfolding between veins.

*Margin.*—Irregular crenate.

*Texture.*—Leathery and pubescent on both surfaces, especially along veins.

*Ribs and veins.*—Distinctly palmate, 5.5 to 7.5 cm long.

*Color.*—Upper side: Mid-green without zonation. Under side: Lighter green color. Ribs and veins not prominently different from upper surface.

*Petioles.*—About 7–13 cm in length.

THE BUD

Size:

*Diameter.*—About 6 mm.

*Length.*—About 1.5–1.8 cm at time of bud opening.

Shape: Pointed tear drop.

Sepals: 5 in number, flat behind petals. Pointed linear lanceolate, 144B RHS with some 53B pigmentation in an open flower.

THE FLOWER

Blooming habit: Continuous throughout the year.

Size: Approximately 4.5 cm diameter, 1.5 cm deep, irregularly radially symmetrical.

Form: Cup shaped when bloom first opens, later flattening to shallow cup shape with maturity.

Petals: 5 imbricate petals, 1.9–2.0 cm wide and approximately 2.8 cm long. The petals are rose (67C-D RHS) with a red splash (57B RHS). Veins slightly darker than interveinal regions. Color changing little with age. Under-side of petals lighter with the veins more prominent and the splash pattern is not present. Petals and petaloids soft and satiny.

Pedicel: Approximately 2.6 cm in length.

Persistence: Flower resistant to shattering.

INFLORESCENCE

Type: An umbel composed of approximately 28 flowers, erect or laterally ascending.

Peduncle: Approximately 14–18 cm in length, green in color.

REPRODUCTIVE ORGANS

Stamens:

*Anthers.*—5–8 positioned below the mature stigma, dull red prior to anthesis.

*Filaments.*—Light pink.

*Pollen.*—Orange in color.

Pistil:

*Number.*—1.

*Length.*—Approximately 8 mm.

*Stigma.*—5 linear lobes of near equal length, curling back toward ovary, purplish-red.

*Style.*—Length: About 6 mm. Color: Purplish red.

*Ovaries.*—At anthesis, densely pubescent with white hairs, oblong. Green drying to a light brown at maturity.

Fruit.—Partially fertile.

I claim:

1. A new and distinct cultivar of geranium substantially as herein shown and described, named Americana Rose Splash, that is characterized by: mid-green foliage without zonation, the flowers are rose with a red splash extending from the center towards the base of each petal, single flower form on large umbels, fast rooting and a robust plant.

* * * * *